United States Patent [19]
Quinlan et al.

[11] Patent Number: 5,941,366
[45] Date of Patent: Aug. 24, 1999

[54] TRANSPORT SYSTEM FOR BIOSPECIMENS

[75] Inventors: Michel G. Quinlan; Stephen J. Wright, both of Peterborough; Edward A. Grant, Kingston, all of Canada

[73] Assignee: Labotix Automation, Inc., Canada

[21] Appl. No.: 08/715,772

[22] Filed: Sep. 19, 1996

[51] Int. Cl.[6] ............................................. B65G 29/00
[52] U.S. Cl. ............................ 198/465.1; 198/867.11; 198/867.13
[58] Field of Search .............................. 198/465.1, 465.2, 198/803.7, 803.14, 867.08, 867.11, 867.13; 422/65

[56] References Cited

U.S. PATENT DOCUMENTS

| | | | |
|---|---|---|---|
| 5,031,749 | 7/1991 | McCoy | 198/465.1 X |
| 5,224,585 | 7/1993 | Blanco et al. | 198/867.13 |
| 5,417,922 | 5/1995 | Maskin et al. | 198/465.2 X |
| 5,484,052 | 1/1996 | Pawloski et al. | 198/867.11 X |
| 5,657,856 | 8/1997 | von Froreich | 198/867.13 X |
| 5,730,276 | 3/1998 | Itoh | 198/465.1 |

FOREIGN PATENT DOCUMENTS

| | | | |
|---|---|---|---|
| WO9625712 | 8/1996 | WIPO | G06F 17/00 |
| WO9636437 | 11/1996 | WIPO | B01L 9/06 |

*Primary Examiner*—James R. Bidwell
*Attorney, Agent, or Firm*—Fitzpatrick, Cella, Harper & Scinto

[57] ABSTRACT

A tansport system for biospecimens includes a conveyor including a conveyor each divided into two or more lanes by lane dividers means. Specimen carriers, each carrying one biospecimen container, include a base which engages the conveyor to transport the biospecimen container and at least three retainer members which are biased together to accept and retain the biospecimen container on the carrier. A variety of traffic control devices, such as diverters and singulators, as well as other control mechanisms such as orientation rails and orientation rollers are combined into control stations to manage the transport of the biospecimens through the system.

10 Claims, 7 Drawing Sheets

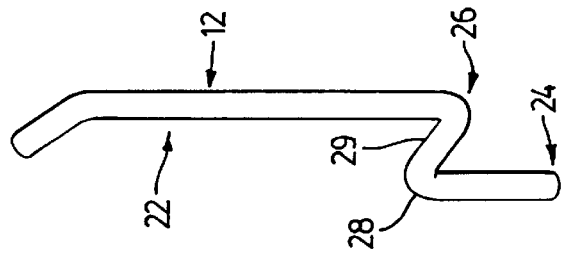
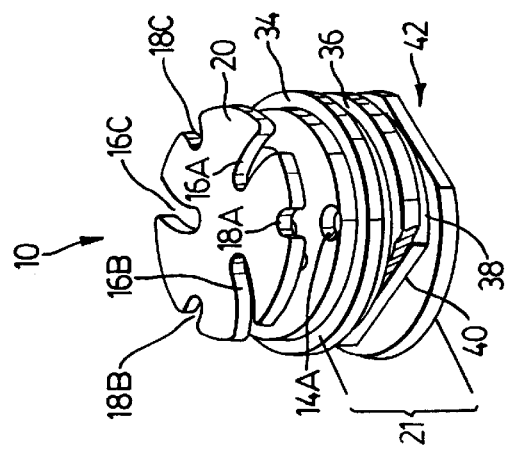
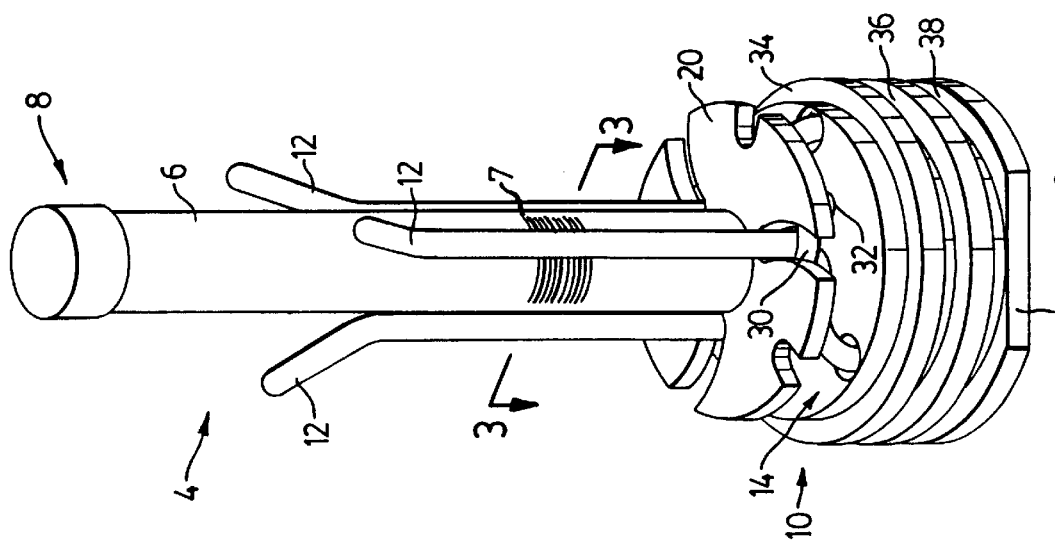

TRANSPORT SYSTEM FOR BIOSPECIMENS

FIELD OF THE INVENTION

The present invention relates to a transport system for transporting biospecimens. More specifically, the present invention relates to a transport system for transporting individual biospecimen containers with a conveyor.

BACKGROUND OF THE INVENTION

Biospecimens, such as blood or urine, are routinely obtained from patients and brought to laboratory facilities for testing and analysis. In general, a patient's biospecimen is placed in a container, such as a test tube or vial, which is then sealed and delivered to the testing laboratory.

Typically, a lab technician at the testing laboratory will manually load these containers, which can vary in their outside dimensions, into specimen container racks, each rack typically holding several containers which can be transported between various locations in the laboratory, as a group, via a conveyor. Individual biospecimens are identified within the group and generally within the laboratory by a bar code or other machine readable indicia affixed to the container. Usually, these indicia are attached to the container prior to or when the specimen is obtained from a patient, however they may be applied when containers are received by the technician in the laboratory. A laboratory information system, or other suitable specimen management means, is employed to also relate the indicia with the test or tests to be performed on the biospecimen.

Once the racks are loaded, they are placed on a conveyor and transported to various stations within the laboratory, such as biospecimen test equipment sites, etc.

The above described prior art biospecimen transport systems have several disadvantages. First, to accommodate containers of different sizes, the container racks are designed with container receptacles which are sized to receive the largest contemplated container. Containers of less than the largest size can therefore move within their respective container receptacles in the rack and this can result in the bar codes or other identifying indicia on the containers being obscured from a scanner reader by portions of the rack. This can require that the containers being removed from the rack each time access is required to the indicia.

Another disadvantage is that several containers of biospecimens are transported along the conveyor as a group in the same rack. This grouped transport of biospecimens can decrease the efficiency of the transport system because transport of all of the biospecimens in a rack is delayed while any single container from the rack is tested, or otherwise accessed, at any location on the transport system. This delay is exacerbated if a particular container contains a biospecimen that must undergo a test that requires a relatively long period of time to complete.

Attempts have been made to improve transport efficiency and/or reduce transport delays by having the lab technician sort the biospecimens and load biospecimens to be tested with similar tests into the same rack. However, this requires a substantial time commitment on the part of the technician to perform the sorting, increasing the expense of operating the laboratory.

SUMMARY OF THE INVENTION

It is an object of the present invention to provide a novel transport system for biospecimens which obviates or mitigates at least one disadvantage of the prior art.

According to a first aspect of the present invention, there is provided a transport system for biospecimens, comprising:
  a conveyor having a conveyor surface arranged in at least two transport lanes;
  a specimen carrier to removably receive and transport a single biospecimen container in one of said two lanes, said carrier including means, to inhibit tipping of said biospecimen container with respect to said conveyor interface.

According to another aspect of the present invention, there is provided a specimen carrier for transporting a biospecimen container on a conveyor, comprising:
  a base member having a transport surface to engage the surface of a conveyor and having stabilization means to inhibit tipping of said container when on said conveyor;
  at least three retainer members rotatably mounted to said base member on a side opposite said transport surface to define a biospecimen container reception site between said retainer members, said retainer members being biased toward each other to receive and maintain a biospecimen container inserted therebetween at said reception site.

According to yet another aspect of the present invention, there is provided a transport system for biospecimens, comprising
  a plurality of specimen carriers, each carrying a biospecimen container;
  a conveyor divided into at least two transport lanes in which said plurality of specimen carriers may be transported;
  a control station comprising at least one traffic control means to control movement of said plurality of specimen carriers in said transport system.

According to yet another aspect of the present invention, there is provided a singulator to space specimen carriers on a conveyor in a transport system, comprising:
  a gate including a blocking portion and a specimen carrier engagement portion; and
  a drive means to rotate said gate to engage a specimen carrier upstream of said gate on said conveyor in said engagement portion and to rotate said gate to move said engaged specimen carrier to a position on said conveyor downstream of said gate wherein said engaged specimen carrier is released from said engagement portion for further movement on said conveyor, said blocking portion preventing specimen carriers upstream of said gate from moving downstream.

According to yet another aspect of the present invention, there is provided a diverter to transfer specimen carriers between two lanes of a conveyor in a transport system, comprising:
  an actuator arm including a cam surface; and
  a drive means to rotate said actuator arm into or out of a first lane in said conveyor from which a specimen carrier is to be transferred, wherein said actuator arm is rotated to abut a specimen carrier in said first lane to direct said specimen carrier to a second, adjacent lane in said conveyor.

BRIEF DESCRIPTION OF THE DRAWINGS

Preferred embodiments of the present invention will now be described, by way of example only, with reference to the attached Figures, wherein:

FIG. 1 shows a perspective view of a specimen carrier carrying a biospecimen container in accordance with an embodiment of the present invention;

FIG. 2 shows a perspective view, partially broken away, of a base member and a retainer member of the specimen carrier of FIG. 1;

FIG. 6A shows a top view of a control station in accordance with an embodiment of the present invention and several specimen carriers moving there through;

DETAILED DESCRIPTION OF THE INVENTION

Figure 3A:
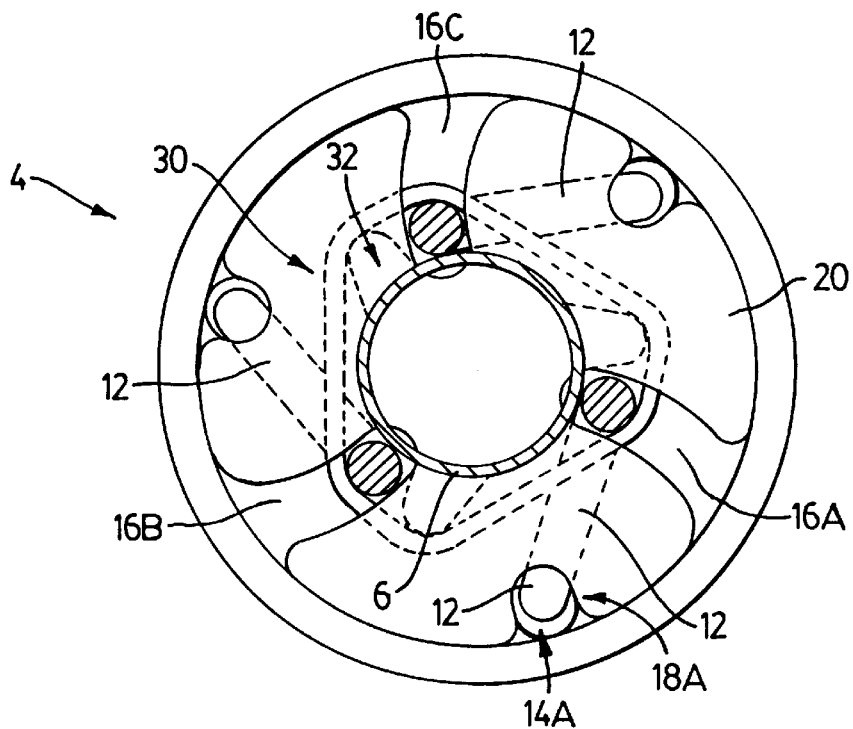
FIG. 3A shows a cross-sectional view through the line 3—3 of FIG. 1.

A specimen carrier in accordance with an embodiment of the present invention is indicated generally at 4 in FIG. 1. Specimen carrier 4 is carrying a test tube 6 with bar code 7 and is sealed by stopper 8. Presently in diagnostic medicine, the containers used to hold biospecimens vary in size and configuration, but the most common configuration is a glass vial. such as test tube 6. which is closed with a seal, such as stopper 8. However, both the height and the diameter of such containers do vary and diagnostic laboratories must deal with a variety of sizes of biospecimen containers.

Specimen carrier 4 comprises a base member 10, which has a generally cylindrical shape, and three retainer members 12. FIG. 2 shows a more detailed view of base member 10 and one of the three retainer members 12. Base member 10 has an upper control plate 20 and a lower base 21, the upper control plate 20 maintained in place by a support 32 (best seen in FIGS. 3A and 3B). Control plate 20 has three arcuate, generally radial grooves 16A, 16B, 16C and three short notches 18A, 18B, and 18C. Base 21 has three sockets 14A, (14B and 14C are not shown) which are positioned under each of a corresponding one of notches 18A, 18B, and 18C.

Each retainer member 2 has an upper end 22 and a lower end 24 and bends 26 and 28 which define an arm 29 therebetween. Each retainer member 12 is installed in specimen carrier 4 by positioning upper end 22 away from the center of base 21 and inserting lower end 24 into socket 14, via notch 18. When lower end 24 is inserted into socket 14 sufficiently such that arm 29 is below the lower surface of control plate 20, retainer 12 is rotated to place upper end 22 into arcuate groove 16. This procedure is repeated for the other two retainer members 12. One of the contemplated advantages of the present invention is that, even in the circumstance wherein one of the retainer members 12 covers a portion of the indicia on the biospecimen container, the width of the retainer member 12 is small enough that the indicia may still be reliably scanned.

Figure 3B:
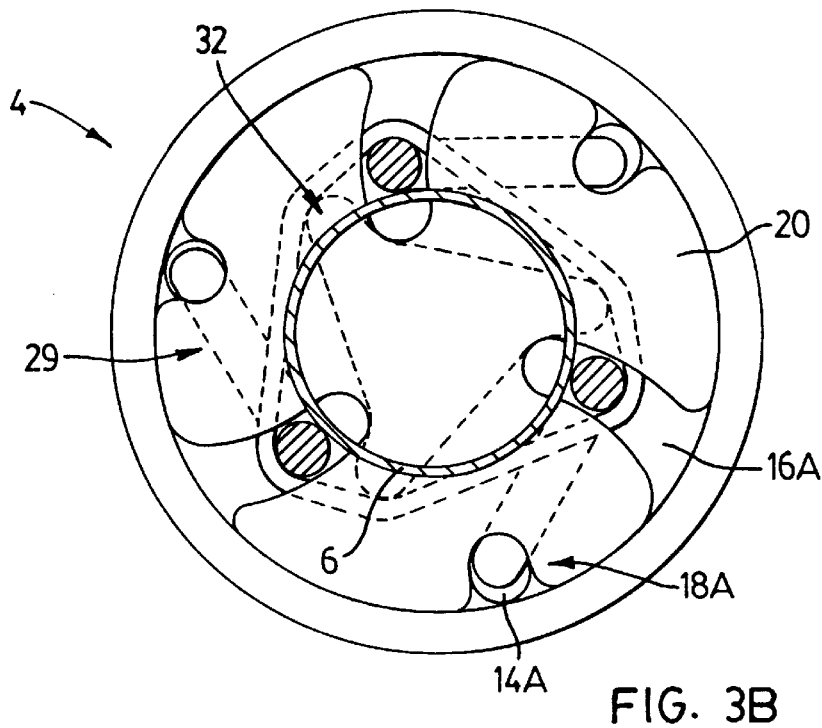
FIG. 3B shows a cross-sectional view similar to that of FIG. 3A wherein a larger diameter biospecimen container is being carried.

A biasing means, for example an O-ring 30, is positioned around upper ends 22 of retainer members 12, below control plate 20. As best shown in FIGS. 3A and 3B, the biasing means urges each retainer member 12 toward the innermost end of its corresponding groove 16. Thus a test tube 6 which is inserted between retainer members 12 is retained there. As shown in FIGS. 3A and 3B, a wide range of diameters of test tubes cam be accommodated by specimen carrier 4.

It is contemplated that the arcuate shape of grooves 16 promotes both the easy insertion of test tubes 6 of various diameters between retainer means 12 and the reliable maintenance of those test tubes between retaining means 12. It is also contemplated that more than three retaining means 12 may be desired in some circumstances, for example to receive non-round containers or very large or very small diameter test tubes, and the modification of specimen car 4 to include four or more retainer means 12 will now be readily apparent to those of skill in the art.

As shown in FIGS. 1 and 2, base member 10 has an upper annular edge 34, a first groove 36, and a second groove 38 which extend about the circumference of base member 10. Base member 10 also has an orientating surface 42, which extends along a portion of the bottom edge of base 21.

First groove 36 and second groove 38 are provided to enhance the engagement of specimen carrier 4 by manipulator devices, such as the grip of a robot arm (not shown), as will be described in more detail below. It is preferred that each of first groove 36 and second groove 38 have a pair of diametrically opposed engagement flats to allow simple engagement of a manipulator device. One of the engagement flats of groove 38 is shown at 40 in FIG. 2. It is contemplated that, with this groove and engagement flat configuration, a manipulator device need only have a slot, such as a U-shaped slot, with an appropriate width to engage one of grooves 36 or 38 with the parallel sides of the slot abutting the engagement flats, to securely lift or otherwise manipulate specimen carrier 4.

Also in a preferred embodiment, specimen carrier 4 is constructed with the pair of engagement flats of one or both of grooves 36 and 38 orientated at preselected angular relationship to orientating surface 42, as will be described below in more detail. It is contemplated that, in many circumstances, only a single grove (either 36 or 38) will be desired, but the presence of two grooves is presently preferred to allow for the transfer of specimen carrier 14 from one manipulator device to another, each of which can engage a respective groove to allow for a 'hand-off' of a specimen carrier 4 between manipulators.

In a presently preferred embodiment, base member 10 is manufactured from Delrin and retainer members 12 are manufactured from stainles steel. It is however contemplated that specimen carrier 4 can be manufactured from other materials, such as for example nylon, polyethylene, stainless steel for base member 10 and high strength or composite reinforced plastic for retainer members 12. Further, depending upon the maximum contemplated height of test tube 6, the maximum contemplated mass of the contents of test tube 6, etc., specimen carrier 4 can include a weight (not shown) in base member 10 to lower the center of gravity of specimen carrier 4.

It is also contemplated that in some circumstances it may be desired to include an identification means on specimen carriers 4 to operate in conjunction with, or instead of, the indica on the biospecimen container carried by the specimen carrier. While it is contemplated that a bar code can be employed as this identification means, it is presently preferred to employ a programable magnetic identification system such as the Idesco Microlog, told by Idesco Engineering, 6940 Wei, Germany. This system includes a magnetic identification device which can be embedded in base member 10 and read by in appropriate reader to uniquely identify a specimen carrier 4.

Figure 4:
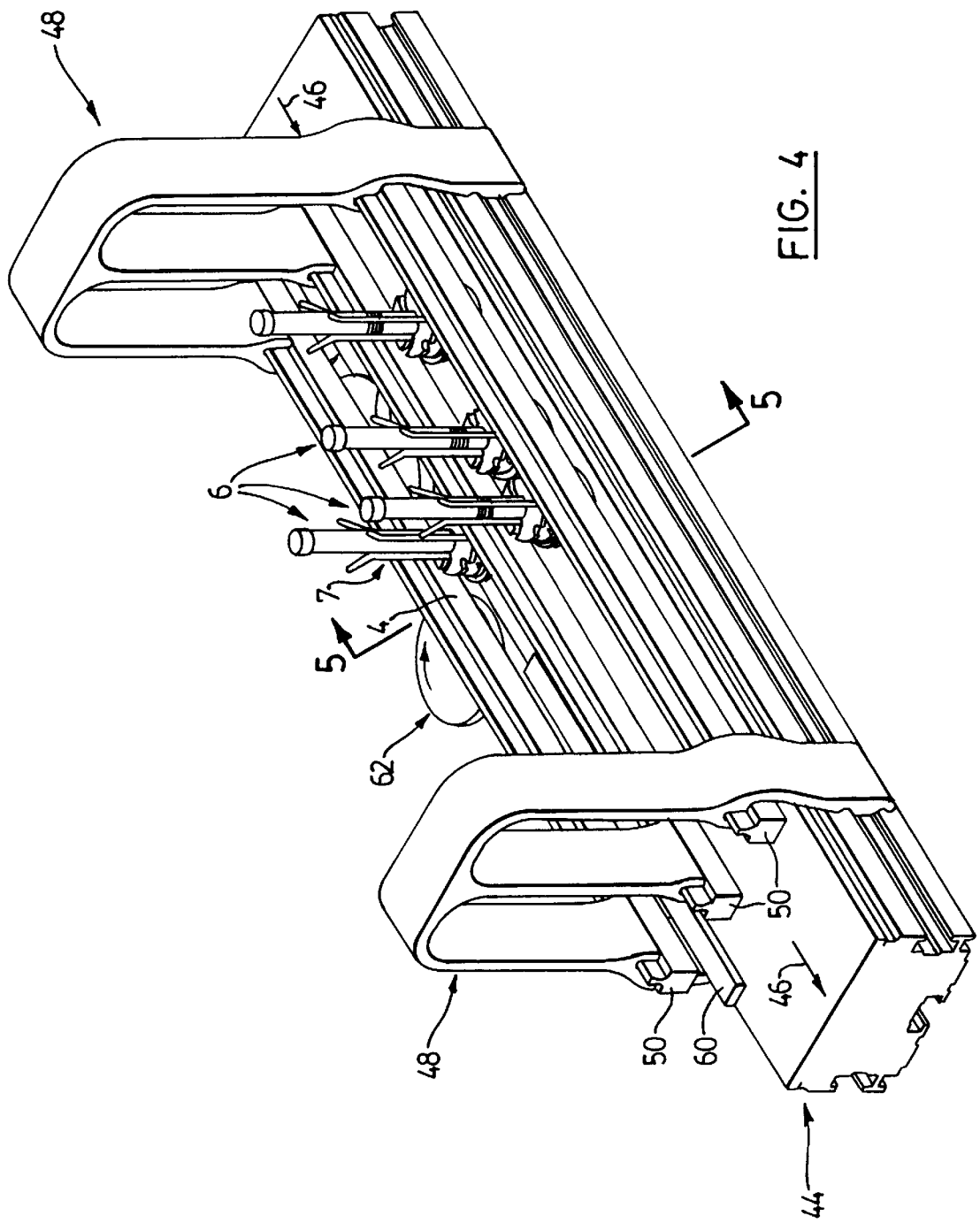
FIG. 4 shows a perspective view of a portion of a conveyor in accordance with the present invention and several specimen carriers thereon.
Figure 5:
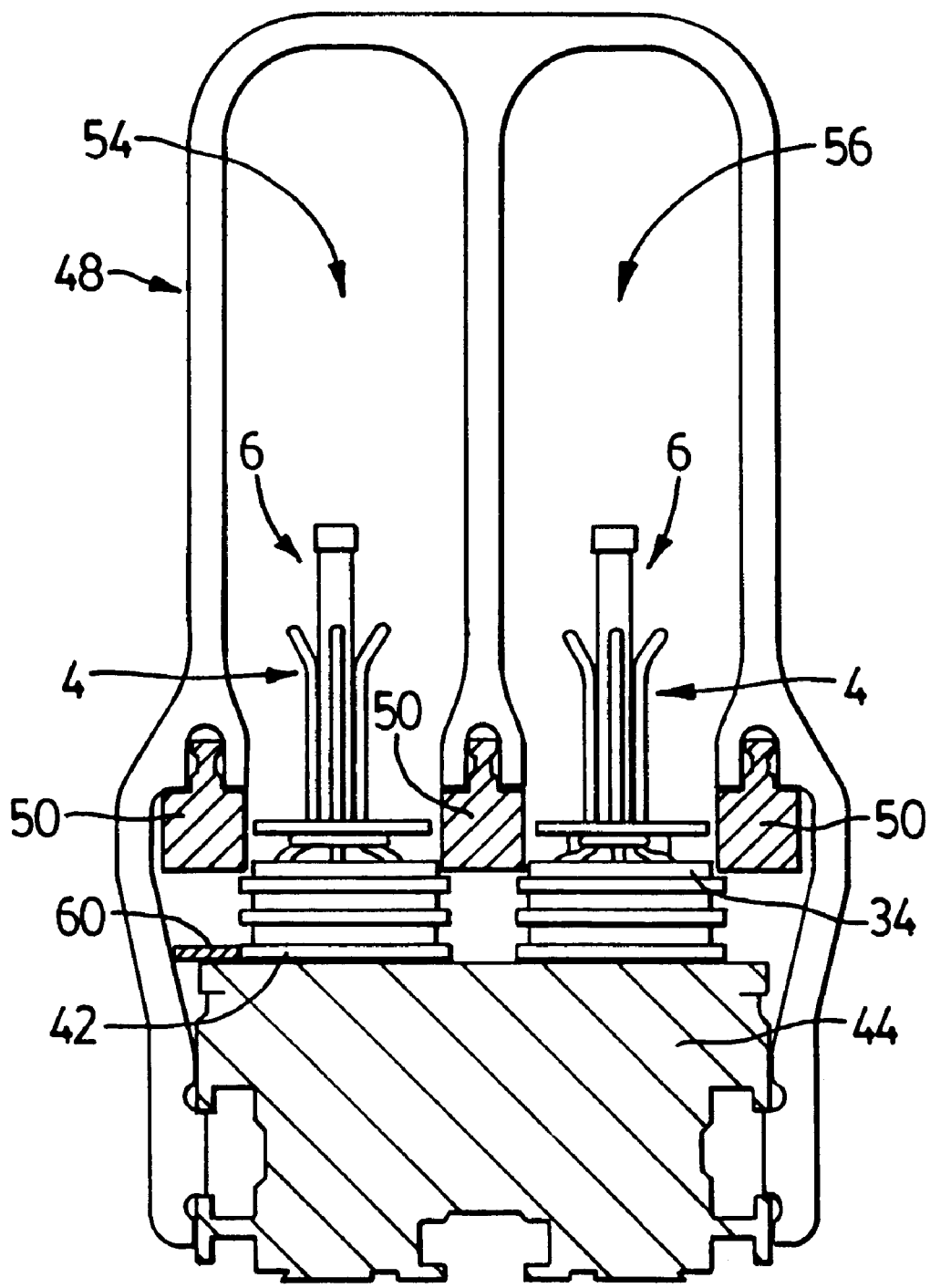
FIG. 5 shows a section through line 5—5 of FIG. 4.

FIGS. 4 and 5 show four specimcen carriers 4 carrying test tubes which are being transported on a moving conveyor 44 in a direction 46. Conveyor 44 can be any suitable conveyor track and in a presently preferred embodiment of the invention is a conveyor sold by Simplimatic Engineering Company, Lynchburg Va., USA as their Simpli-Flex Modular Conveyor System. As shown in the Figures, conveyor 44 is divided into two lanes 54 and 56 by lane definition means, which in one embodiment of the invention comprise a series of arches 48 each of which retains three spaced support rails 50, one adjacent the outer edge of each lane, and one located at the midpoint between the other two. Arches 48 are fixed with respect to conveyor 44 and retain the support rails 50 at a preselected height above the surface of conveyor 44. Each support rail 50 is equidistant from its adjacent support rails 50 to define lanes of equal width, and the rails extend along the length of conveyor 44 which can include straight and curved runs.

As shown in FIG. 5, arches 48 maintain the spacing between adjacent support rails 50 at a slightly wider than the width of specimen carrier 4 at upper annular edge 34 so that upper annular edge 34 slidably engages the lower surface corner of the support rails 50 which define the lane it is in. This engagement of upper annular edge 34 with rails 50 inhibits tipping of specimen carrier 4 while moving on conveyor 44 and is referred to herein as stabilizing means.

The support rail 50 which is located between and divides two adjacent lanes can include discontinuities at various points along the length of the conveyor 44 to permit individual specimen carriers to be moved sideways from a first lane 54 to a second lane 56 or vice versa, as will be described further below. Further, the outermost support rails 50 may have similar discontinuities to permit specimen carriers to be removed from or replaced on a lane of conveyor 44.

It is contemplated that support rails 50 can be made from aluminum or any other suitable material as will occur to those of skill in the art. Similarly, arches 48 can be made from aluminum or other suitable materials provided that the resulting combination of support rails and arches is sufficiently rigid that rails 50 prevent tipping of specimen carriers 4. It has been found that, when support rails 50 and arches 48 are fabricated from aluminum, a sufficiently rigid stucture is obtained with respect to conveyor 44 when adjacent arches 48 are spaced at three foot interval.

In some circumstances, it may be desired to have a conveyor 44 with more than two lane. In such cases, conveyor 44 can be wider and arches 48 can be fabricated to retain more than three support rails, thereby dividing a conveyor into more than two lanes.

As discussed earlier, base member 10 has a planar orientating surface 42 which extends along a portion of the bottom edge of base 21. FIGS. 4 and 5 show an orientation rail 60 which is fixed to conveyor 44, such that it is just above the working surface of the conveyor. During transportation of a specimen carrier 4 by the conveyor, the orientating surface 42 abuts orientation rail 60. and with the above-mentioned stabilizing means maintains the orientation of specimen carrier 4 with respect to conveyor 44.

Orientation rail 60 need only be present in locations on conveyor 44 wherein it is desired to have specimen carriers 4 in a known orientation, as will described below. Accordingly, if orientation rails 60 are only located at various points about conveyor 44, an orientation roller 62 is provided adjacent the upstream end of each orientation rail 60 to facilitate the engagement of orientating surface 42 to orientation rail 60. Orientation roller 62 frictionally engages base member 10 of a specimen carrier 4 causing the specimen carrier 4 to rotate with respect to the adjacent orientation rail 60 and the movement of conveyor 44 urges specimen carrier 4 downstream once the orientating surface 42 is aligned with orientation rail 60.

Orientation of a specimen carrier 4 can be desired for a number of reasons, the most common of which is to position the machine readable indicia on test tube 6 into a known position. Generally, a test tube 6 having a bar code 7 is loaded into a specimen carrier 4, by suitable means, with bar code 7 in a specific orientation with respect to orientating surface 42. Specimen carrier 4 then is placed on conveyor 44 and transported as desired. When it necessary to read bar code 7, an orientation rail 60 is provided adjacent bar code scanner and an orientation roller 62 rotates the specimen carrier to engage orientating surface 42 with orientation rail 60 to position the bar code for scanning.

Figure 6A:
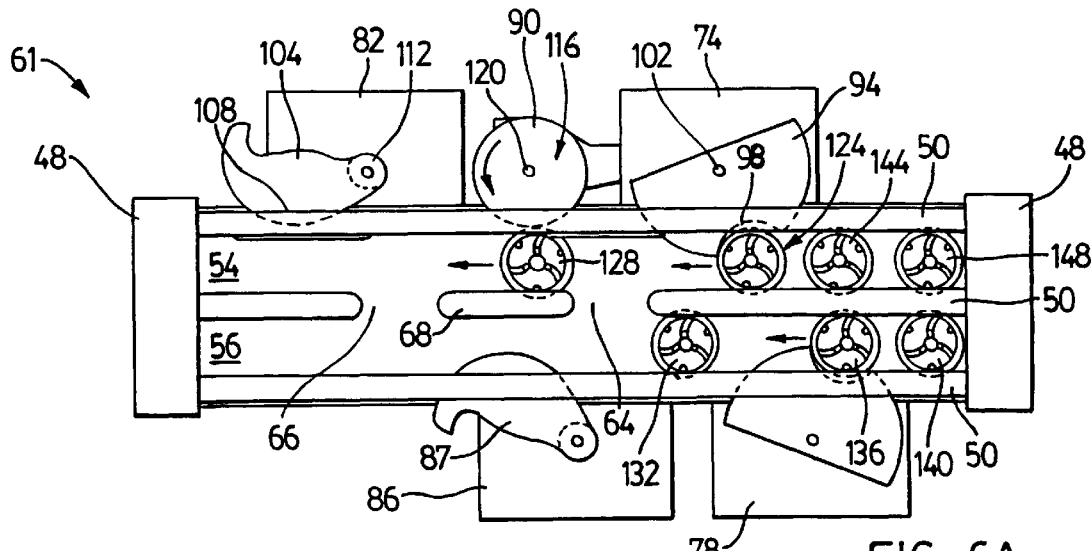
Figure 6B:
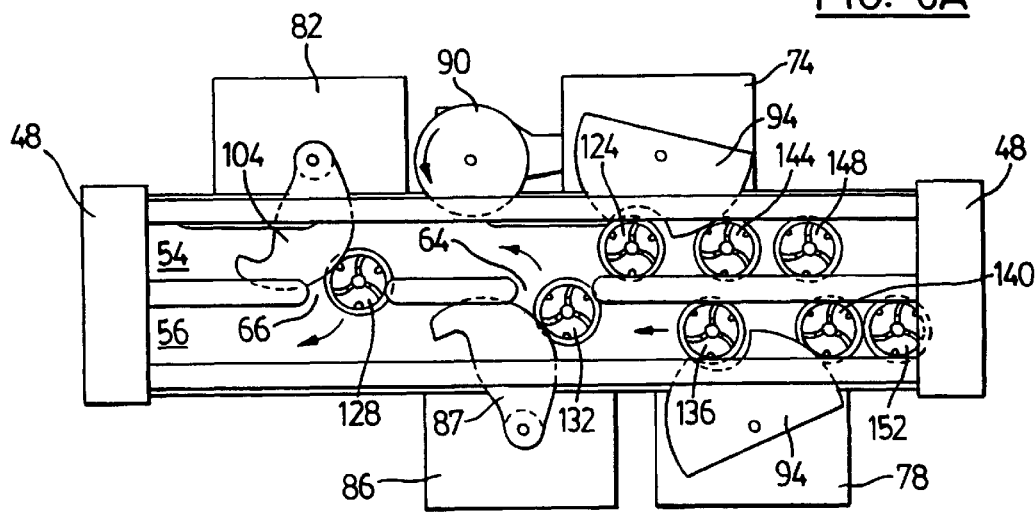
FIG. 6B show a top view of the control station of FIG. 6A at a later point in time.
Figure 6C:
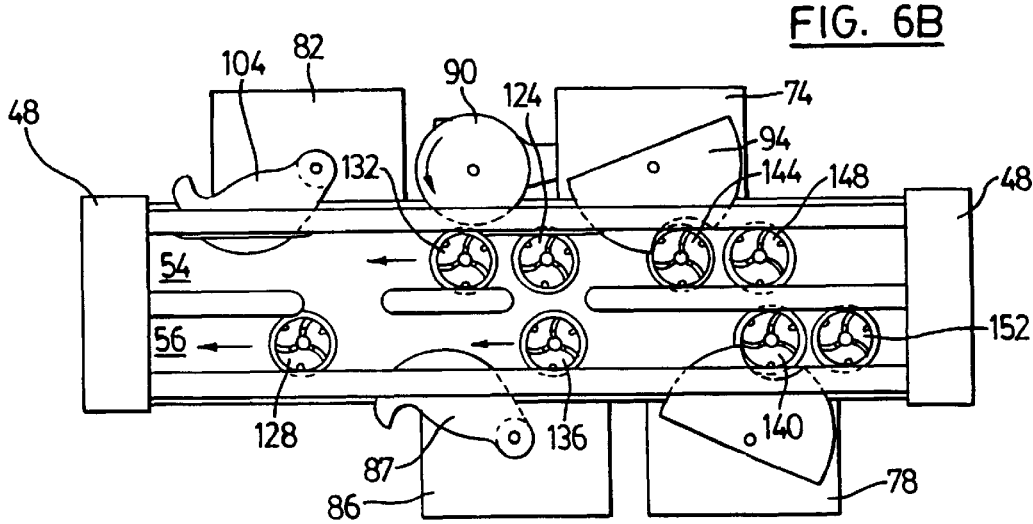
FIG. 6C shows a top view of the control station of FIG. 6 at a later point in time.

FIGS. 6A, 6B and 6C show a control station 61 for use with conveyor 44. The particular control station 61 shown in these Figures provides for the identification of specimen carriers 4 and their conditional exchange from lane 54 to lane 56 and vice-versa. As shown, the support rail 50 between lanes 54 and 56 has two discontinuities 64 and 66 that are sized to permit movement of a specimen carrier 4 between lanes 54 and 56. The arch 48 which supports a segment 68 of the center support rail 50 is not shown in these Figures for clarity.

Control station 61 includes traffic control devices, specifically two singulators 74 and 78 and two diverters 82 and 86. Singulators 74 and 78 each operate to separate a group of specimen carriers 4 arriving at the singulator in a lane of conveyor 44 into single, spaced, specimen carriers 4 which may continue travel on conveyor 44 or otherwise be further processed.

While singulator 74 is described herein in more detail, it will be understood by those of skill in the art that the construction and operation of singulator 78 only differs from the discussion of singulator 74 in that it operates on specimen carriers arriving in lane 56. Singulator 74 comprises a substantially senmi-circular shaped gate 94 having a cutout 98, Gate 94 can be fabricated from any suitable material such as aluminum, plexiglass, etc. as will be understood by those of skill in the art. Gate 94 is attached to the axle 102 or a suitable drive means which can be any suitable method of rotating gate 94 through about 270 degrees or more of rotation, and in a presently preferred embodiment, this drive means is a dc motor. A suitable control means, not shown, operates the drive means to move gate 94 as desired.

Cutout 98 has a shape which is complementary to the shape of base member 10 of specimen carriers 4 and singulator 74 is mounted adjacent conveyor 44 to permit gate 94 to extend below the support rail 50 and into lane 54 as shown in the Figures.

In operation, one or more specimen carriers (124, 144 and 148 accumulate in a lane of conveyor 44 upstream of singulator 74 with the specimen carrier 124 closest to singulator 74 being received in cutout 98 a shown in FIG. 6A.

When it is desired to permit specimen carrier 124 to continue past singulator 74, gate 94 is rotated to the position shown in FIG. 6B, thus releasing specimen carrier 124 from cutout 98 for continued movement along conveyor 44. As shown in the Figure, the curved portion of gate 94 blocks the next specimen carrier 144 from movement along conveyor 44. Gate 94 is then rotated back to the position shown in FIG. 6C wherein specimen carrier 144 engages cutout 98. The time intervals between iterations of this process are selected to provide the desired spacing of specimen carriers on conveyor 44 and can be used to stagger the arrival of specimen carriers 4 at stations on conveyor 44.

As will be understood by those of skill in the art, singulators 74 and 78 are also capable of operatig as blocking gates, i.e. to prevent movement of upstream specimen carriers past traffic control or other stations when gates 94 are in the position shown in FIG. 6B. If desired, gates 94 can also be rotated such that the flat surface opposite cutout 98 is adjacent support rail 50. In this position (which is nut shown in the Figures) the gate does not extend into the adjacent lane and lane is "open" for free movement of specimen carriers past the singulator.

Diverters 82 and 86 operate to transfer specimen carriers 4 between lanes 54 and 56 through corresponding discontinuities 66 and 64. While diverter 82 is described herein in more detail, it will be understood by those of skill in the art that the construction and operation of diverter 86 only differs from that of diverter 82 in that it operates to transfer specimen carriers 4 from lane 56 to lane 54.

Diverter 82 comprim a cam-shaped actuator 104 which is mounted at 112 to a drive means, not shown. Actuator 104 can be constructed from any suitable material, such as aluminum or plexigiass, as will he undergeood by those of skill in the art. The drives means for actuator 104 can be any suitable drive mechaism as will also be understood by those of skill the art and, in a presently preferred embodiment, is a dc motor. Actuator 104 has a cam surface 108 which is shaped to abut and move specimen carriers 4 from the lane in which the diverter is located, through the corresponding dincontinuity, and into the adjacent lane. Diverter 82 is mounted adjacent conveyor 44 to permit actuator 104 to extend into lane 54, rotate below support rail 50 and abut the base member 10 of specimen carriers 4.

In FIG. 6A, specimen carrier 128 is approaching diverter 82 and is to be transferred from lane 54 to lane 56. Actuator 104 of diverter 82 is shown in FIG. 6A in it's fully retracted position wherein cam surface 108 does not extend into lane 54. When it is desired to transfer specimen carrier 128 from lane 54 to 56, actator 104 of diverter 82 is rotated to extend into lane 54, as shown in FIG. 6B, and cam urace 108 and thk continued movement of conveyor 44 cooperate to move specimen carrier 128 through discontinuity 66 to lane 56 as shown iu FIGS. 6H and 6C. After a lane change has been effected. actuator 104 is retracted to its start position.

The particular configuration of control station 61 is intended to examine and sort specimen carnes arrving in lanes 54 and 56. Specifically, an indicia reading means, which is not shown in FIGS. 6A through 6C for clarity, is located adjacent lane 52 between singulalor 74 and diverter 82 to read the indicia on the test tubes on specimen carriers 4. In a presently preferred embodiment of the invention, the indicia reading means is a bar code scanner which inerfaces with a specimen management system, such as a laboratory information system.

When a bar code scanner is employed as indicia reading means, it can be desired to rotate the specimen carrier 4, and the test tube on it, with respect to the bar code scanner to enhance scanning of the bar code. Accordingly, a rotator 90 is provided which comprises wheel 116 and a drive means 120. Wheel 116 is mounted adjacent to conveyor 44 and extends underneath support rail 50 to engage rotate the base member 10 of an oncoming specimen carrier 4 to rotate the specimen carrier about its vertical axis.

In control station 61, singulators 74 and 78 are operable to allow one specimen carrier 4 at a time to be examined by the indicia reading means. Specimen carriers 4 arriving on lane 56 are, after release from singulator 78, transferred to lane 54 by diverter 86 for scanimng by the indicia reading means. Specimen carriers 4 arriving on lane 54 travel directly from singulator 74 to the indicia reading means. Singulator 74 and 78 cooporate to ensure that only a single specimen carrier 4 is to be read by the indicia reading mean at one time.

When the indicia reading means has examined the indicia on the test tube on the specimen carrier 4 being scanned, the laboratory information system or other specimen management system determines on which lane the specimen carrier 4 should leave control station 61 and diverter 82 is operated accordingly.

In FIGS. 6A through 6C, a specimen carrier 124 which arrived on lane 54 is scanned by the indicia reading means and transferred to lane 56 for exit from control station 61. Specimen carrier 132 which arrived on lane 56 is transferred to lane 54 (FIG. 6B) for scanning by the indicia reading means and, depending upon the need of the specimen management system, can exit control station 61 via either lane 54 or 56.

Figure 7:
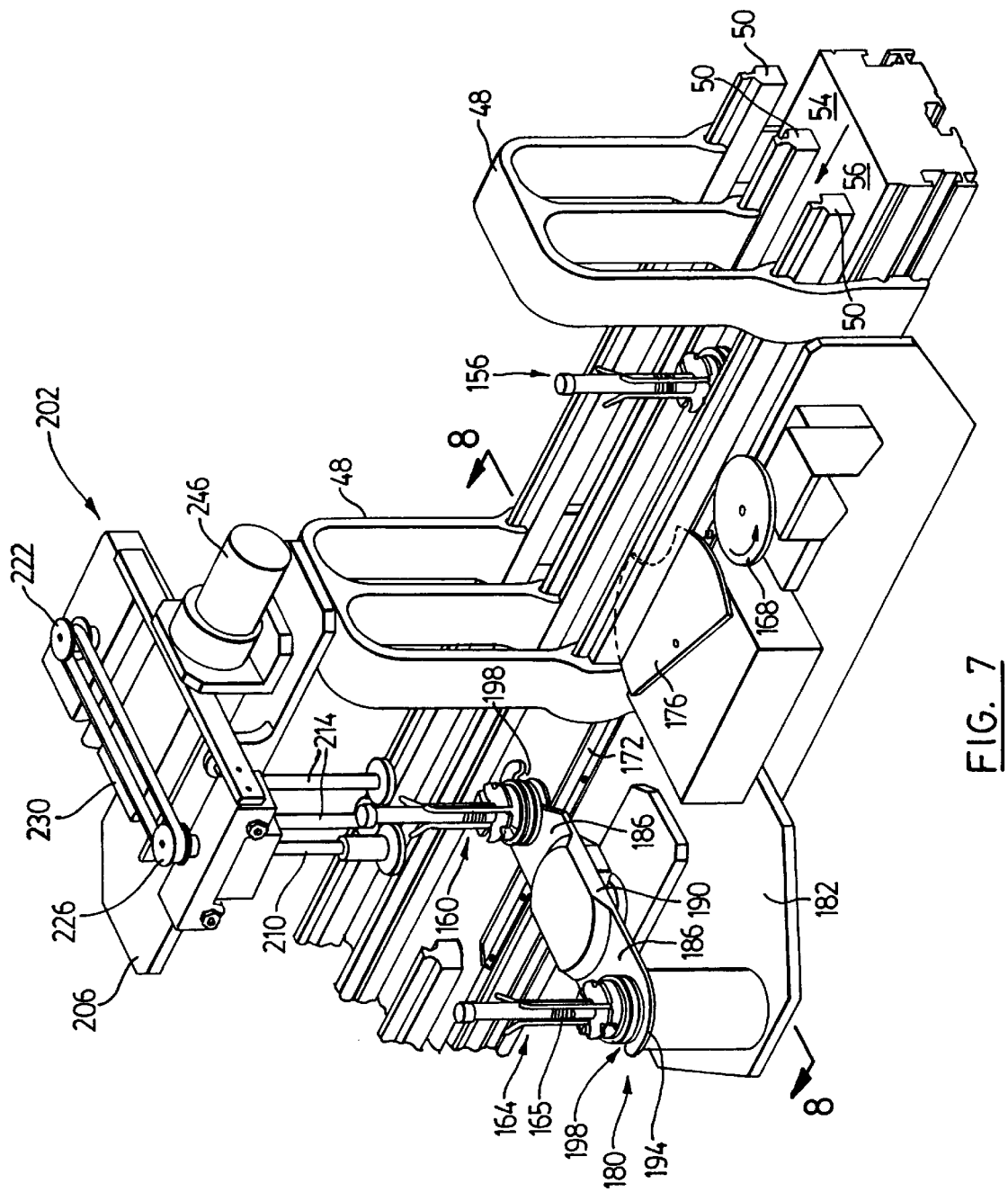
FIG. 7 shows a perspective view of another control station in accordance with an embodiment of the present invention.
Figure 8:
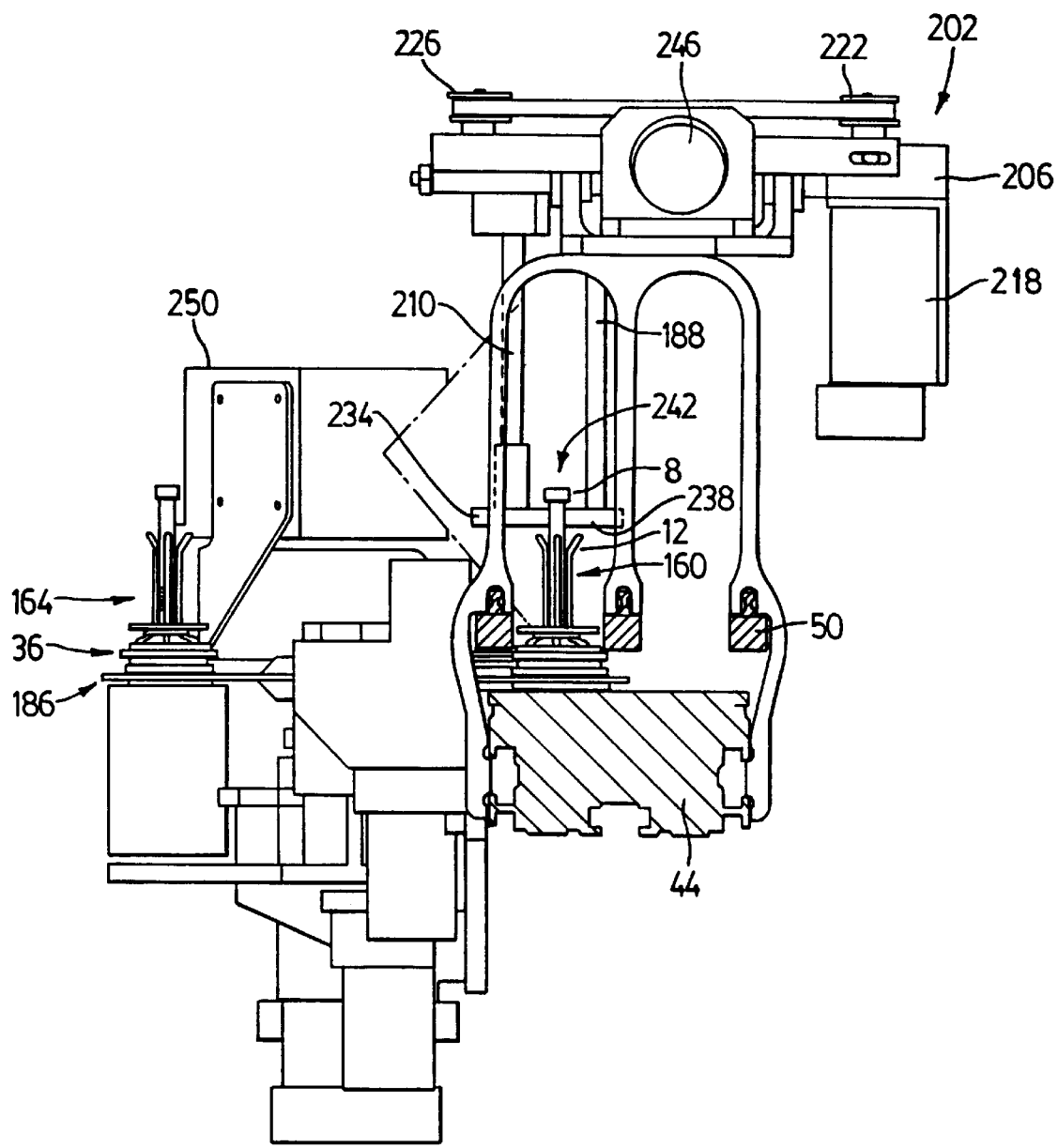
FIG. 8 shows a section taken along line 8—8 of FIG. 7 and including a barcode scanner not shown in FIG. 7.

FIG. 7 and FIG. 8 illustrate another control station 200 in accordance with the present invention. In those Figures, conveyor 44 is shown transporting specimen carriers 156, 160. and 164 and each specimen carrier is carrying a test tube marked with an identifying bar code 165. In FIG. 7, specimen carriers 156, 160 and 164 are transported by conveyor 44 from right to left. An orientation roller 168, similar to orientation roller 62 in FIG. 4, rotates the specimen carriers to engage an orientation rail 172, similar to orientation rail 60 iscdussed in detail earlier, thereby fixing the rotational orientation of the specimen carriers with respect to the orientation rail 172. A singulator 176. ensures that only single specimen carriers, such as specimen carrier 160, travel down conveyor 44 to the specimen carrier handling means, described below.

A specimen carrier handler means for selectively remnoving and/or placing a specimen carrier on conveyor 44 is shown as handler 180. Handler 180 includes an rotor arm 186 and a motor means 190, such as a de servo motor, to rotate rotor arm 186. Rotor arm 186 includes two grips 194 which are both spaced an equal radius from motor means 190. Grips 194 each have a substantially U-shaped cutout 198 which is arranged such that, when cutout 198 is over lane 56 of conveyor 44, the parallel sides of cutout 198 are parallel to support rails 50. Orientating roller 168 and orientation rail 172 cooperate to ensure that specimen carriers 156, 160 and 164 approach handler 180 with the engagement flats in groove 38 parallel to support rails 50.

Cutouts 198 arm sized to engage groove 38 of a specimen carrier, with the paralle sides of cutout 198 engaging the engagement flats of groove 38 thereby preventing the specimen carrier from rotating in cutout 198. In FIGS. 7 and FIG. 8. cutouts 198 of rotor 190 have engaged groove 38 of specimen carriers 160 and 164.

In operation a specimen carrier. such as specimen carrier 160, is released by singulator 176 and travels along conveyor 44 to rotor arm 186. Groove 38 of specimen carrier 160 engages cutout 198 in one end of rotor arm 186 as shown in FIG. 7 and a test tube rotating means 202 engages the test tube.

Specifically, test tube rotating means 202 includes a chassis 206, a driven roller 210 and two idler rollers 214. A motor means 218 is mounted to chassis 206 and drives driven roller 210 via a belt drive comprising pulleys 222 and 226 and drive belt 230. Idler rollers 214 rotate freely on suitable bearings. Drive roller 210 and idler rollers include suitable contact surfaces 234 and 238 to frictionally engage the outer surface of test tube 242 carried by specimen carrier 160.

Test tube rotating means 202 has two positions, all open position and a rotate position. FIGS. 7 and FIG. 8 show the tube rotwor 202 in the rotate position wherein drive roller 210 and idler rollers 214 are in engagement with the test tube. In the open position, drive roller 210 and idler rollers 214 are spaced away from each other to permit test tube 242 to enter or exit from the area between drive roller 210 and idler rollers 214.

In the illustrated rotate position, drive roller 210 is rotated by motor 246 thereby rotating test tube 242 rmative to specimen carrier 160, which is pevented from rotating by cutout 198 or rotor arm 186. A bar code scanner, identified at 250 in FIG. 8, reads the bar code 165 on the test tube. In addition to allowing bar code 165 to be scanned. test tube rotating means 202 allows the test tube to be oriented, relative to the base member 10 of a specimen carrier such that the bar code is in a known position.

Rotor 180 allows test tubes carried on specimen carriers to be removed from or placed on conveyor 44. Specifically, a specimen carrier can be placed in or removed from cutout 198 when in the manipulating position occupied by specimen carrier 164 in the Figures. Rotor 180 rotates as needed to transfer specimen carriers between lane 56 and the manuipulating position.

The removal and replacement of a specimen carrier can be accomplished in any suitable manner including, by a laboratory technician or by a robot manipulator which engages groove 36. It is also contemplated that in some circumstances it may be desired to remove or load a test tube from or on a specimen carrier in the manipulating position. For example, the test tube of specimen carrier 164 can be removed by a conventional robot and empty specimen carrier 164 returned to conveyor 44 for subseqcnt recovery and reuse. Similarly, a test tube can be loaded into an empty specimen carrier in the manipulating position in any suitable manner. In this latter case, it is contemplated that test tube rotating means 202 will be employed to orientate bar code 165 with respect to base member 10, prior to releasing the specimen carrier for continued transport by conveyor 44 downstream of control station 200.

It will be understood by those of skill in the art that a variety of other control stations can be constructed from the components described herein and with others without departing from the scope of the present invention.

The above-described embodiments of the invention are intended to be examples of the present invention and alterations and modifications may be effected thereto, by those of skill in the art, without departing from the scope of the invention which is defined solely by the claims appended hereto.

We claim:

1. A transport system for biospecimens, comprising:
  a conveyor having a conveyor surface arranged in at least two transport lanes; and
  a specimen carrier to removably receive and transport a single biospecimen container in one of said two lanes, said carrier including
    a base member having a transport surface to engage said conveyor surface;
    means to inhibit tipping of said biospecimen container with respect to said conveyor surface, said means to inhibit tipping comprising a surface on said base member which engages a portion of said conveyor; and
    at least three support members rotatable mounted to said base member and extending therefrom opposite said transport surface defining a biospecimen container reception site, said support members being biased toward each other to receive and maintain a biospecimen container therebetween at said reception site.

2. A transport system according to claim 1 wherein said lanes include an orientating surface and said base member includes at least one orientation element to engage said orientating surface and thereby place said specimen carrier in a preselected orientation.

3. A transport system for biospecimens as defined in claim 1 wherein said lanes are defined between rails and said portion of said conveyor is an edge of at least one of said rails.

4. A transport system for biospecimens according to claim 3 wherein said support members rotate through an accurate path as they receive said biospecimen container.

5. A transport system for biospecimens as defined in claim 3 wherein said biasing means is a resilient member encircling said support members.

6. A transport system according to claim 2 wherein ssid bas member includes at least one engagement groove to enable a manipulator to engage said specimen carrier.

7. A transport system according to claim 6 wherein said at least on engagement groove includes an orientation surface.

8. A specimen carrier for transporting a biospecimen container on a conveyor, comprising:
  a base member having a transport surface to engage the surface of a conveyor and having stabilization means to inhibit tipping of said container when on said conveyor;
  at least three retainer members rotatably mounted to said base member on a side opposite said transport surface to define a biospecimen container reception site between said retainer members, said retainer members being biased toward each other to receive and maintain a biospcecimen container inserted therebetween at said reception site.

9. A specimen carrier according to claim 8 wherein said base member includes an orientation means to orient said base member with respect to said conveyor.

10. A specimen carrier according to claim 8 wherein said base member includes at least one groove to be engaged by a manipulator.

* * * * *